United States Patent [19]

Lichte

[11] Patent Number: 5,303,585
[45] Date of Patent: Apr. 19, 1994

[54] FLUID VOLUME SENSOR

[75] Inventor: Leo J. Lichte, Riverside, Calif.

[73] Assignee: JTL Medical Corporation, Riverside, Calif.

[21] Appl. No.: 785,792

[22] Filed: Oct. 31, 1991

[51] Int. Cl.$^5$ ............................................. G01F 23/28
[52] U.S. Cl. ................................. 73/290 V; 73/149; 367/908
[58] Field of Search ............... 73/149, 290 V, 290 B, 73/114; 367/908; 364/564, 509, 571.07

[56] References Cited

U.S. PATENT DOCUMENTS

| | | | |
|---|---|---|---|
| 3,163,843 | 12/1964 | Dieckamp | 73/290 V |
| 3,237,451 | 3/1966 | Haeff | 73/290 V |
| 3,326,042 | 6/1967 | Ross et al. | 73/290 V |
| 3,520,186 | 7/1970 | Adams et al. | 73/290 V |
| 3,603,149 | 9/1971 | McKown | 73/290 V |
| 3,839,651 | 10/1974 | Michaels | 73/295 |
| 3,918,018 | 11/1975 | Tuley et al. | 73/295 |
| 4,063,457 | 12/1977 | Zekulin et al. | 73/290 V |
| 4,144,517 | 3/1979 | Baumoel | 73/290 V |
| 4,170,765 | 10/1979 | Austin et al. | 73/290 V |
| 4,221,004 | 9/1980 | Combs et al. | 367/114 |
| 4,320,659 | 3/1982 | Lynnworth et al. | 73/290 V |
| 4,474,061 | 10/1984 | Parker | 73/290 V |
| 4,535,627 | 8/1985 | Prost et al. | 72/149 |
| 4,572,253 | 2/1986 | Farmer et al. | 367/908 |
| 4,623,976 | 11/1986 | Carp et al. | 364/571.07 |
| 4,651,555 | 3/1987 | Dam . | |
| 4,733,381 | 3/1988 | Farmer et al. | 367/93 |
| 4,912,686 | 3/1990 | Craster | 73/290 V |
| 4,991,433 | 2/1991 | Warnaka et al. | 367/908 |
| 5,027,655 | 7/1991 | Sweet | 374/290 V |

FOREIGN PATENT DOCUMENTS

| | | | |
|---|---|---|---|
| 231518 | 11/1960 | Australia | 73/290 V |
| 3703658 | 8/1988 | Fed. Rep. of Germany | 73/290 V |

Primary Examiner—William A. Cuchlinski, Jr.
Assistant Examiner—G. Bradley Bennett
Attorney, Agent, or Firm—Knobbe, Martens, Olson & Bear

[57] ABSTRACT

A volume sensing system includes electronic circuitry which is electrically connected to an ultrasonic transducer. The transducer is affixed by means of an adaptor to the base of a container having a known configuration. The container holds a liquid and a gas so that a liquid-gas boundary is formed within the container. The transducer generates ultrasonic pulses which propagate through the liquid, are reflected at the liquid-gas boundary, and are received again by the transducer. The received return pulse is converted into an electrical signal which is analyzed by the electronic circuitry to determine the level of the liquid within the container. The level of the liquid within the container is then employed to determine the volume of the liquid within the container in accordance with the configuration of the container. In a preferred embodiment, the adaptor includes an indicator which may be used to identify the configuration of the container.

9 Claims, 6 Drawing Sheets

FLUID VOLUME SENSOR

BACKGROUND OF THE INVENTION

The present invention relates to volume sensors for determining the volume of a fluid in a container. More particularly, the present invention relates to volume sensors of the type adapted for the continuous computation of the volume of liquid remaining in a container.

In a variety of applications, it is desirable to be able to determine at any given moment the remaining volume of fluid in a container. Examples in the medical field range from determining the remaining reagent in a source container for use in automated clinical instrumentation to remaining saline or other fluid volume in an intravenous infusion.

A variety of means have been devised in the past for permitting an attending physician or staff member to estimate a remaining fluid volume. In the most basic form, containers have been provided with transparent walls and a graduated scale which is visible from the outside. However, visual observation of fluid level is not always practical, such as when the container is not readily locatable within the clinician's view. In addition, in some applications it may be desirable to have a more precisely quantitative indication of remaining fluid level or volume, or the fluid volume data may be desirably utilized to trigger electronics such as alarm limits, pumps or other devices which add and/or drain fluid from the container, or other data processing activities.

Thus, there have been devised a variety of electronic fluid level detectors in the prior art. For example, U.S. Pat. No. 4,063,457 to Zekulin, et al. discloses an ultrasonic sensing device for mounting within a storage vessel such as a bilge or railroad tank car. The sensing device comprises an elongate tubular body to be vertically oriented within the tank car, having a port at the lower end to allow fluid to enter the tube and rise to the level of fluid in the remaining tank. Spaced apart vertically within the tube are a series of pairs of piezo-electric transducers which serve as transmitters and receivers of ultrasonic energy. Because ultrasonic energy propagates more readily through liquid than through air, the system can determine which pairs of piezo-electric transducers are below the fluid level and which pairs of piezo-electric transducers are above the fluid level. Thus, each piezo-electric pair serves to determine simply the presence or absence of fluid at that level.

Another submersible probe-type liquid level indicator is disclosed in U.S. Pat. No. 3,163,843 to Dieckamp. In this device, mechanical vibrations are propagated axially from a transducer through the probe which extends vertically within the fluid to be measured. Reflected transverse pulses are created at both the liquid surface and the submerged distal end of the probe, which are smaller in amplitude than the applied pulse. These reflected transverse pulses are propagated back to the transducer, and the waveforms of the various pulses are evaluated on an oscilloscope to determine the fluid level.

Another approach is disclosed in U.S. Pat. No. 4,144,517 to Baumoel. That patent discloses an externally mounted single transducer liquid level detector in which the presence or absence of liquid at a particular location of a tank or pipe is sensed through the wall of the container. The transducer may be secured to the outer surface of the container, such as by hand pressure, clamping or cementing. By comparing the rate of decay of the test signal following multiple wall reflections to known rate of decay values for filled and empty regions of the container, an output signal is produced which indicates the presence or absence of liquid in the container adjacent the transducer location.

Notwithstanding the foregoing, there remains a need for a volume sensor device which can be externally mounted to the container and which can provide remaining fluid volume data on a continuous basis from empty through full.

SUMMARY OF THE INVENTION

The present invention is an apparatus for determining the volume of a liquid within a container having a known configuration or total volume wherein a boundary exists between the liquid and a gas or other media. The apparatus comprises a transducer in sonic communication with the container for generating and subsequently receiving an ultrasonic signal. Circuitry is in electrical connection with the transducer for measuring the time elapsed between the generation and reception of the ultrasonic signal.

The apparatus further comprises circuitry for converting the elapsed time between the generation and reception of the ultrasonic signal into distance data representing the distance from the transducer to the boundary between the liquid and the gas. Means for determining volume data representing the volume of the liquid is included wherein each value of the volume data is determined from a value of the distance data or a value representing the time elapsed between the generation and reception of the ultrasonic signal. In a preferred embodiment, the means for determining the volume data comprises a look-up table memory and/or a central processing unit.

The invention preferably further includes a host computer and control circuitry which allow for the control of a number of different functions such as audible and visual alarms; a pump, to permit the filling and/or draining of the container; valves that allow for the control of flow; and a printer, that can provide a hard copy of all past activities that the volume sensing system has completed, or print them as the activity occurs.

The present invention also provides a method for determining the volume of a liquid within a container having a known configuration or total volume wherein a boundary exists between said liquid and a gas or other media. An ultrasonic signal is generated, propagated through the liquid, and subsequently received by a sensing device. The time elapsed between the generation and reception of the ultrasonic signal is then measured and converted into volume data representing the volume of the liquid within the container.

In accordance with a further aspect of the invention, an adaptor is provided as an interface between a container and a transducer. The adaptor is formed to affix to a container of a unique configuration so that each adaptor type may be used only in connection with a container having the corresponding unique configuration. In one embodiment, the adaptor includes electronics or like means which serve to identify the type of adaptor as well as the configuration of the container to which the adaptor corresponds.

These and additional features and advantages of the present invention will become apparent from the Detailed Description of Preferred Embodiments which follows, considered together with the drawings and claims.

DETAILED DESCRIPTION OF PREFERRED EMBODIMENTS

In accordance with one aspect of the present invention, an ultrasonic sound signal is utilized to detect the interface between liquids and gas (air or any other gaseous media) in the desired container. It is known that certain solid materials and liquids have varying permeability to certain frequencies in the ultrasonic sound range, but gases are relatively impermeable to sound waves in this frequency range. This phenomenon forms the basis of the known ultrasound-based fluid level detectors.

Figure 1:
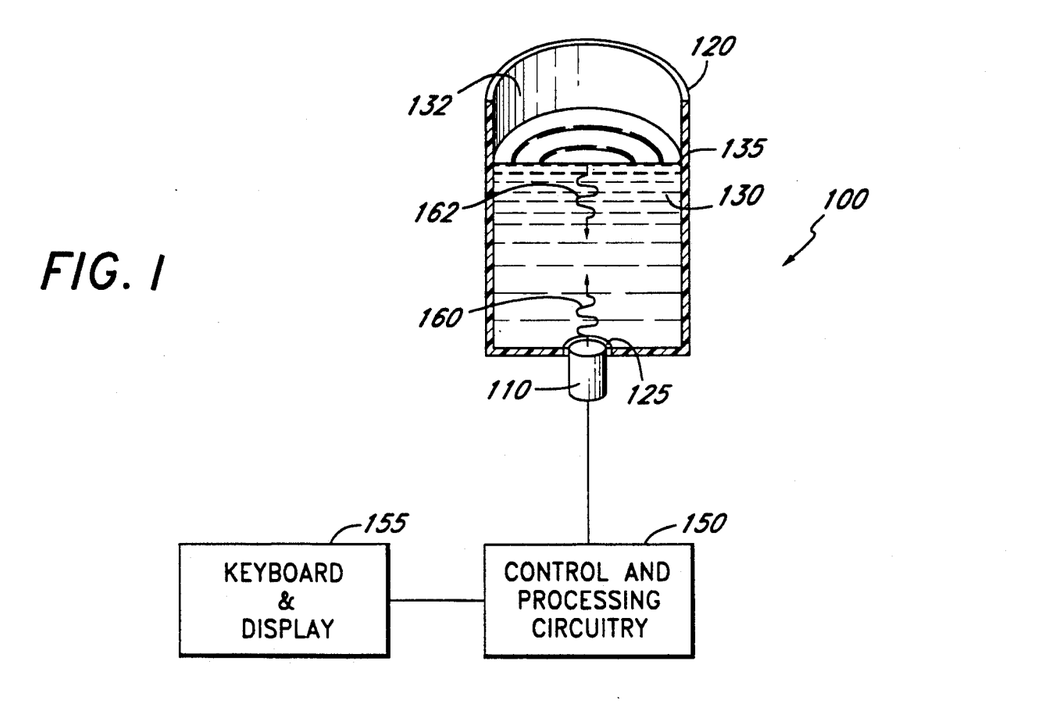
FIG. 1 is a simplified schematic diagram which shows the basic configuration of a volume sensing system constructed in accordance with the present invention.

FIG. 1 is a simplified schematic diagram which shows the basic configuration of a volume sensing system 100 constructed in accordance with the present invention. The volume sensing system 100 includes an ultrasonic transducer 110 which is affixed to the base of a container 120 by means of an adaptor 125. The container 120 is constructed to hold a liquid 130. The liquid 130 does not fill the entire volume of the container 120, and a gas 132 (e.g., air) is present which fills the remaining volume within the container 120, so that a gas-liquid boundary 135 is formed within the container 120. The transducer 110 is electrically connected to control and processing circuitry, which is functionally designated by the control and processing circuitry box 150 (the control and processing circuitry 150 will be described in greater detail with reference to FIGS. 5 and 6 below).

In a preferred embodiment, the control and process circuitry 150 includes a microprocessor or other processing device which may be connected with a keyboard and display interface 155, or a dedicated system in the medical instrument so that a user may program and/or manually interact with the system 100. Thus, the volume sensing system 100 may act as a "stand alone" module. In one embodiment, the control and process circuitry 150 may be connected to a host computer system (not shown) such as an IBM PC, AT, etc., which may be employed to provide additional storage and/or interface capability.

The transducer 110 is utilized to generate ultrasound pulses 160 and detect reflected pulses 162 from the liquid-gas interface boundary 135, and may be produced in any of a variety of ways, which will be understood by one of skill in the art. In one embodiment, a ceramic crystal (not shown) is encased in a protective material such as epoxy to provide the transducer assembly 110. Suitable ceramic crystals are obtainable from EDO Corporation Electro-Ceramic Division, and sold under the Model number AD-1259-.325; material: EC-70 Type V. The contacting face of the transducer 110 is approximately one-half inch in diameter in one embodiment.

In order to hold the crystal securely within the transducer housing, any epoxy having minimal or optimally no gaseous inclusions may be employed. It has been found, however, that the performance of the crystal may be slightly improved by forming a small air gap within the epoxy directly behind the crystal.

The transducer assembly 110 is attached to the bottom of the container 120 in such a way that the side of the crystal that oscillates (face) is in sufficient sonic communication with the container 120 to provide an ultrasonic coupling. This contact can be achieved by permanent means or temporary means, as long as the material used to obtain that contact contains minimal or no gaseous inclusions. Materials having gaseous inclusions, such as foamed materials, tend to dampen propagation of the signal. In addition, where clamping means are used in place of the epoxy, a coupling medium layer such as glycerine or silicone oil may also be used, as well as flexible materials such as elastomers and rubber may also be used, as is known in the art.

Although the adaptor 125, container floor, and any other media which separates the crystal face from the liquid 130 can be any of a wide variety of materials, materials should optimally be selected having sufficient acoustic qualities that they do not excessively dampen the ultrasonic pulse 160 as it propagates through the materials. Ideally, the natural frequency of the crystal is to be about 2.0 to 2.5 megahertz, although frequencies in the range of 1 megahertz to 5 megahertz may have applications.

The electronic circuitry 150 is provided to excite the crystal at a known frequency for short pulses, as is well known in the art. By applying a voltage across the crystal at the proper frequency, the crystal is excited so that it vibrates in accordance with an effect known as the piezoelectric effect. This vibration produces the sharp ultrasonic pulse 160. The pulse 160 is then coupled through the container 120 and into the liquid 130.

The transducer 110 receives control signals from the circuitry 150 which cause the transducer 110 to emit the ultrasonic pulse 160. In one embodiment, the frequency of the emitted pulse 160 is advantageously on the order of 3 MHz. The pulse 160 propagates vertically through the liquid 130, but generally does not propagate well through the gas 132. Instead, most of the ultrasonic energy of the pulse 160 is reflected back from the liquid-gas boundary 135 so that the "echo" pulse 162 is created. For example, as shown in FIG. 1, the pulse 160 is an example of an ultrasonic pulse which has just been generated by the transducer 110, while the pulse 162 is an example of an ultrasonic "echo" pulse which has been reflected from the liquid-gas boundary 135.

The "echo" pulse 162 propagates back through the liquid 130 to the transducer 110, where the pulse 162 is detected and converted into an electrical signal. In order to prevent interference between the propagated and reflected ultrasonic pulses 160, 162, the pulse 160 should have a dwell time sufficient to allow the transmitted pulse 160 to return (bounce) off of the liquid-gas boundary 135 and be received by the same crystal after generation of the same pulse 160 has ceased, and before a new pulse is generated.

When the crystal receives the returned "echo" pulse 162, it reacts by oscillating. The oscillation of the crystal is then converted to a voltage signal readable by the electronic circuitry 150. The voltage signal is transmitted to the circuitry 150 where it is analyzed and processed to determine the volume of the liquid 130 within the container 120.

When determining the volume of the liquid 130 within the container 120, the duration between the transmittal of the pulse 160 and the reception of the reflected return pulse 162 is measured. If the velocity of the transmitted ultrasonic pulse 160 is known, the measured duration can be converted into a distance value which represents the distance that the pulse traveled. The distance value can be converted into a number of different value units such as inches or centimeters, etc., or simply an internal, machine-readable value. The measurement of the duration between the transmittal and reception of the ultrasonic pulse 160, as well as the conversion of the measured duration into a distance value is advantageously accomplished by means of the control and processing circuitry 150.

As stated above, when the velocity at which the ultrasonic pulse 160 propagates through the liquid 130 is known, the distance between the liquid-gas interface 135 and the transducer 110 can be calculated using the duration measurement. The velocity at which the pulse 160 propagates through the liquid 130 can be determined using a calibration procedure in which a test pulse is generated by the crystal, reflected at the liquid-gas boundary 135, and received by the crystal within the transducer 110. The time between the transmission and reception of the test pulse is then measured. Finally, the actual distance between the crystal within the transducer 110 and the liquid-gas boundary 135 is measured precisely. This measured distance, of course, would also take account of the thickness of any solid material that is used to attach the transducer 110 to the container 120 and/or the thickness of the container material.

The velocity of an ultrasonic pulse within the fluid 130 may then be calculated using the measured values of the time between the transmission and reception of the test pulse, and the measured distance between the crystal and the liquid-gas boundary 135. By means of this calibration technique, variations in the propagation velocity of the pulse 160 due to temperature changes in the liquid 130, composition changes of the liquid 130, etc., may be accounted for. Once a calibrated pulse propagation velocity value has been obtained, the distance value may be calculated by simply multiplying the velocity value by half of the duration value.

Since velocity varies as a function of both temperature and fluid density, accuracy is optimized if calibration occurs under conditions which are similar to the actual use environment. In one preferred application of the present invention, the invention is utilized to determine fluid volume in a reservoir for receiving blood drained from the chest cavity of a patient recovering from open heart surgery. The normal physiologic temperature of human blood is approximately 37° C., and open heart surgery is typically conducted at any of a variety of reduced temperatures. In certain procedures, blood or other fluids could be reduced to as low as about 4° C. In addition, when returning blood from a reduced temperature back to 37° C., the blood will frequently be heated slightly above normal to approximately 40° C.

Thus, to accommodate the changes in viscosity which occur over the range of temperatures experienced in this application, the apparatus of the present invention is provided with sensor and circuitry to automatically measure the temperature of the fluid and adjust for the time differences in the propagated signal which occur as a result of changed viscosity at different temperatures. The instrument will typically be calibrated at the point of manufacture throughout the range of from about 2° C. to about 45° C. in approximately 5° increments.

The volume of the container must also be determined. In accordance with the present invention, the volume of the container 120 can be determined from the acquired distance value by a number of different techniques. For example, if the container's exact configuration and dimensions are known, the volume of the container 120 can be determined mathematically as a function of the level of the liquid 130 (i.e., the distance value). If, however, the container 120 is irregularly shaped, the volume of the liquid 130 within the container 120 can be determined empirically by means of a calibration procedure which, in one embodiment, employs a "look-up" table within the circuitry 150.

Figure 2A:
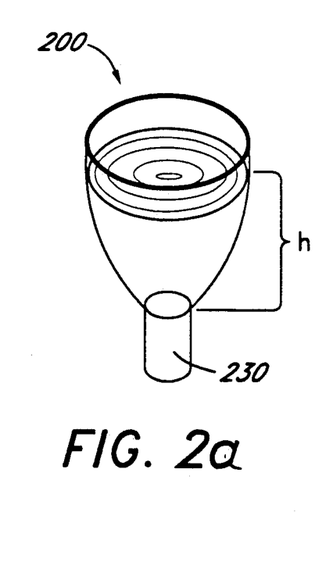
FIGS. 2a–2c show three different regular container configurations having an easily calculable height to volume correlation.
Figure 2B:
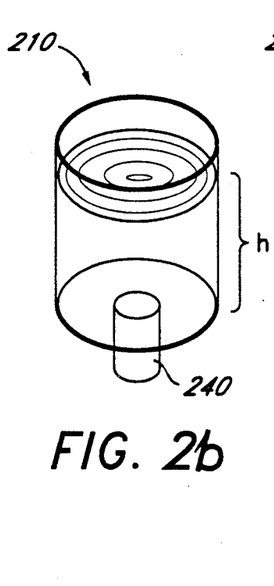
Figure 2C:
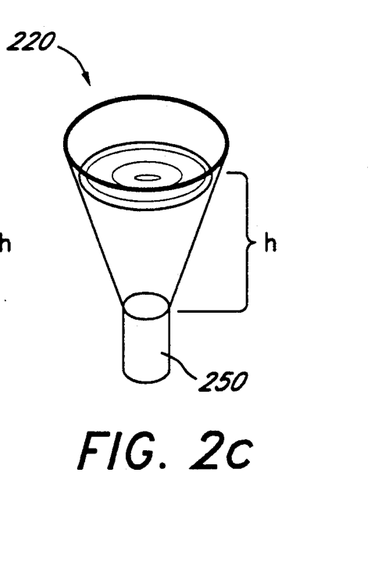

If the container 120 has a known configuration which may readily be described mathematically as a function of the level of the liquid 130, then the appropriate mathematical formula can be programmed into the process and control circuitry 150, and the volume of the liquid 130 within the container 120 can be calculated as a function of the level (or height) of the liquid 130 from the base of the container 120. For example, FIGS. 2a-2c show a variety of different containers 200, 210, 220 each having a different predetermined configuration. As shown in FIGS. 2a-2c, the containers 200, 210, 220 have transducers 230, 240, 250 affixed at their bases respectively, so that the distance between the transducers 230, 240, 250 at the base of each of the containers 200, 210, 220 and the liquid-gas boundaries in each of the containers 200, 210, 220 corresponds to the height, h, of the liquid within each container. Thus, if the level or height, h, of the liquid within each of the containers 200, 210, 220 can be measured, a corresponding volume value can be determined.

For example, if the distance value, h, has been determined for the container 200 having a parabolic cross-section (FIG. 2a), then the volume of the liquid within the container 200 may be calculated as $V = Kh^2 + C$, where K and C are constants which are determined by the exact dimensions of the container 200. K and C may be calculated using conventional Calculus techniques for determining the volume of a solid configured so that its boundaries conform to a known mathematical equation. In the case of the container 210, having a cylindrical configuration (FIG. 2b), the volume of the liquid within the container may be calculated as $V = Ah$ where A is the cross-sectional area of the inside of the base of the container 210. Likewise, if the container 220 having a conical configuration (FIG. 2c) is employed, the volume of the liquid within the container 220 at a height h is calculated as $V = Kh^3 + C$ where K and C are once again determined by the exact dimensions of the container 220. Similarly, the volume of liquid within any number of containers having a known configuration may be determined. Therefore, having obtained the level or height of a liquid in a container of a known configuration and dimension, we can also obtain the volume of liquid that a particular liquid level equates to.

Referring to FIG. 1, if the configuration of the container 120 is such that the increase in height (or depth) of the liquid 130 is consistent with an increase in volume as in the configurations described above, then it is a simple matter of converting each unit of liquid height to volume mathematically. However, many containers are not uniform in configuration, and therefore the height-to-volume conversion is not constant. For example, FIGS. 3a-3c illustrate irregularly shaped containers which may be used in accordance with the present invention.

Figure 3A:
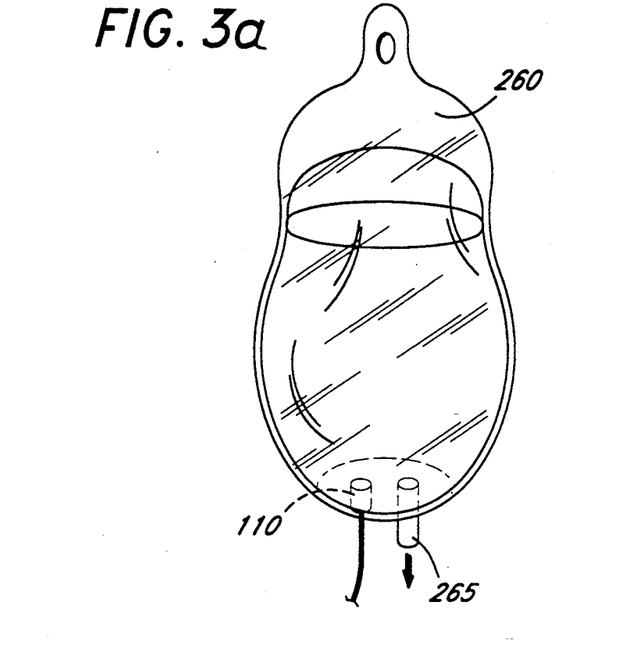
FIGS. 3a–3c show three different irregular container configurations.
Figure 3B:
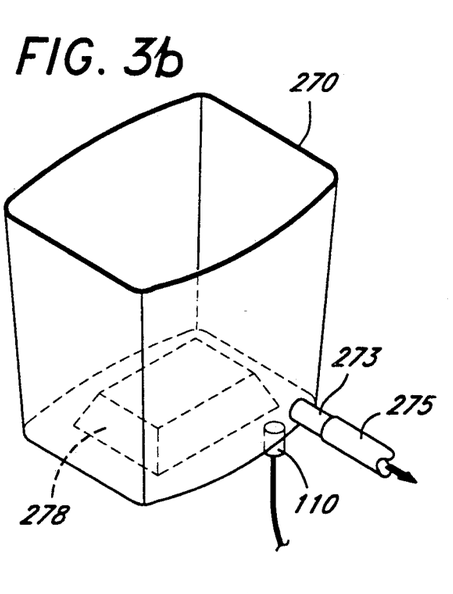
Figure 3C:
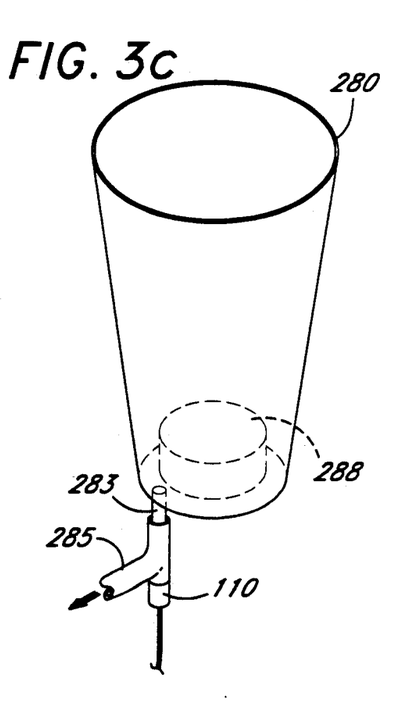

FIG. 3a shows a flexible container 260 (e.g., an IV gravity drip bag) wherein the height of the liquid within the container holds a varying relation to the volume of the liquid within the container. The container 260 includes a fluid outlet tube 265 at its base, and has the transducer 110 affixed proximate to the fluid outlet tube 265. FIGS. 3b and 3c show irregularly shaped containers 270, 280 having configurations which are not readily described mathematically.

The container 270 includes an outlet port 273 on the side of the container 270 at substantially the lowest point of the container 270. The outlet port 273 is in fluid connection with a fluid outlet tube 275 which allows fluid to drain from the container 270. The transducer 110 is affixed to the container 270 proximate to the port 273 so that the transducer 110 is also at substantially the lowest point of the container 270.

Also included within the container 270 is a fluid volume displacer 278. The fluid displacer 278 displaces fluid at the bottom of the container 270 so that the height to volume ratio is increased at the lower portion of the container 270 when the volume of the fluid is low. By increasing the height to volume ratio at the bottom of the container, higher resolution measurements of the fluid level can be made when the volume of the fluid is low.

Referring to FIG. 3c, the container 280 includes an outlet port 283 on the base of the container 280 at substantially the lowest point of the container 280. In the embodiment shown, the outlet port 283 is in fluid connection with a Y-shaped outlet tube 285. The Y-shaped outlet tube 285 has one branch which allows fluid to flow out from the container 280, and another branch which is adapted to receive the transducer 110 so that the transducer 110 is situated directly below the port 283. The container 280 also includes a fluid volume displacer 288 which serves substantially the same purpose as the fluid displacer 278 within the container 270. Due to their irregular configurations, the containers 260, 270, 280 preferably have the correlation of liquid level to liquid volume determined empirically. The control and processing circuitry 150 associated with this volume sensor 100 will incorporate a "look-up" table, which allows the correlation of height (liquid level) to volume to be calculated for irregularly shaped containers 120.

Referring again to FIG. 1, in order to determine the volume of irregularly shaped containers as a function of the determined distance value, a calibration procedure is employed in accordance with one aspect of the invention. When it is desired to implement a new container 120 having an irregular configuration, the transducer 110 is placed in sonic connection with the container 120 by means of the adaptor 125. The user may then manually input information, by means of the keyboard and display 155, which will allow the process and control circuitry 150 to identify the irregularly configured container 120. In one embodiment, the circuitry 150 is able to identify the configuration of the container 120 by means of the adaptor 125. This may be done if it is expected that a container having the same configuration (and consequently the same adaptor) will be used in the future.

Once information identifying the new configuration has been stored within the system 100 memory, the container 120 is completely filled with a known volume of the liquid 130. A test pulse is then generated by the transducer 110, and the duration between transmission and reception of the test pulse is measured. The measured duration value is then stored within the memory of the process and control circuitry 150 in association with a value indicating the known volume of the liquid 130. Thus, the measured duration value may serve as an address value which is used to "look-up" the volume which the measured duration corresponds to.

The level of the liquid 130 within the container 120 is then decreased in small, known increments (e.g., volume increments of 5 milliliters), and the above procedure is repeated after each decrease in volume. Thus, a "look-up" table is formed having incremental duration values corresponding to each increment in volume. During actual operation of the volume sensing system 100, certain duration values will be measured which may not correspond exactly with the incremental duration values obtained. Those measured duration values which do not exactly correspond to the stored incremental duration values can be interpolated, or rounded to the nearest stored duration value, depending upon desired precision. In this way each duration value is associated with a known volume value so that the volume of the liquid 130 within the irregularly shaped container 120 can be determined for a given duration value.

Of course, the parameters of the system 100 may be changed depending upon operating considerations such as the accuracy of volume measurement desired. For example, in order to obtain more accurate volume measurements, the volume increments used in accordance with the above described calibration procedure may be decreased to 1 milliliter or less. Furthermore, it is possible to begin with the container 120 empty and increase the volume of the liquid 130 in known volume increments to create the desired "look-up" table.

It should be noted that when the container 120 approaches empty, or the volume of the liquid 130 is very small, the duration time between the transmission and reception of the ultrasonic pulses 160, 162 becomes very short. If the duration time becomes too short this could cause problems with signal interference between pulses. Namely, the reflected "echo" pulse 162 could return to the transducer 110 before transmission of the pulse 160 is complete. In addition, a shorter duration time may also decrease the accuracy of the system.

Figure 4A:
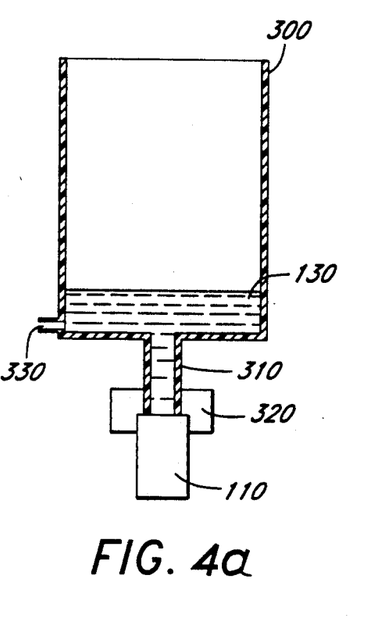
FIGS. 4a and 4b are cross-sectional views of two possible configurations of the container which provide for a longer pulse duration time.
Figure 4B:
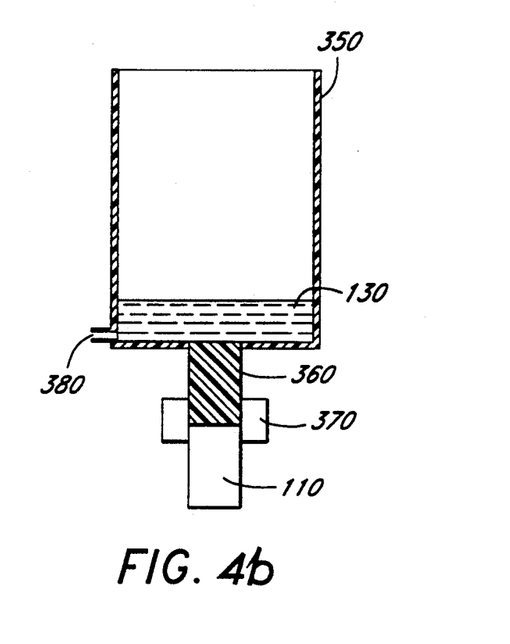

In order to prevent signal interference and retain accuracy of measurement for very small volume levels of the liquid 130 within the container 120, it may be necessary to incorporate certain features into the system 100 which provide for an increased signal duration time. FIGS. 4a and 4b show two alternative embodiments of the system 100 which provide for a longer duration time.

FIG. 4a is a cross-sectional view of a container 300, which holds a small volume of the liquid 130, and includes an extended well 310 at its base. The well 310 is open to the container 300 so that the liquid 130 is able to flow into the well 310. The transducer 110 is affixed to the bottom of the well 310 by means of an adaptor 320, so that the transducer 110 is in sufficient sonic communication with the well 310 to transmit an ultrasonic pulse through the liquid 130 within the well 310. An outlet valve 330 is situated at the base of the container 300, above the bottom of the well 310, so that the liquid 130 within the well 310 is not considered when determining the volume of the liquid 130 within the container 300. This is because, in normal operation, the liquid 130 within the well 310 does not flow out of the container 300, but remains within the well 310, so that it is not useable liquid. Thus, the container 300 is effectively empty when the liquid 130 is present only within the well 310.

When it is desired to determine the volume of the liquid 130 within the container 300, the same general procedure described above with reference to FIG. 1 is employed, except that the height of the liquid 130 is calculated to take account of the height of the liquid 130 within the well 310. Namely, the height of the liquid 130 within the container 300 is determined by measuring the time between the transmission and reception of the pulses 160, 162, converting the measured duration into distance, and then subtracting a distance equal to the length of the well 310. Because the height of the liquid 130 in the well 310 is subtracted out when the effective height of the liquid 130 within the container 300 is determined, the system 100 will indicate that the container 300 is empty when the liquid 130 is present within the well 310 only. In a preferred embodiment, the well 310 is long enough so that the ultrasonic pulses 160, 162 are able to propagate without interference. That is, the length of the well 310 should be such that the time required for an ultrasonic pulse to propagate through twice the length of the well 310 is greater than the dwell time of the pulse 160. Thus, even if the container 300 is approaching "empty," sufficient time will be provided for the pulses 160, 162 to be transmitted and received by the transducer 110 without interference so that accurate remaining volume data may be obtained.

FIG. 4b shows a cross-sectional view of a container 350 which holds a small volume of the liquid 130, and includes an ultrasonically permeable extension 360 at its base. The transducer 110 is affixed to the bottom of the extension 360 by means of an adaptor 370, so that the transducer 110 is in sufficient sonic communication with the ultrasonically permeable extension 360 to transmit an ultrasonic pulse through the extension 360 to the liquid 130 within the container 350. Of course, the extension 360 may be affixed to or integrally formed with the transducer 110 or the container 350. An outlet port 380 is situated at the base of the container 350. The extension 360 may be made of a number of ultrasonically permeable materials which do not significantly dampen ultrasonic pulses, such as ceramic, plastics, or the like.

The extension 360 serves essentially the same purpose as the well 310 in FIG. 4a. That is, the extension 360 provides a sufficient distance through which the pulses 160, 162 may propagate so that, when the container 350 is empty, enough time is provided for the pulses 160, 162 to propagate without interference. Accordingly, the extension 360 should be of such a length and material that the time it takes for an ultrasonic pulse to propagate through twice the length of the extension 360 is greater than the dwell time of the pulse 160. Thus, in the embodiment described in FIG. 4b, sufficient time will be provided for the pulses 160, 162 to be transmitted and received by the transducer 110 without interference when the container 350 is empty. One advantage of the solid extension 360 over the fluid well embodiment is that essentially 100% of the fluid in the container is available for use.

Due to the numerous configurations of containers to which the transducer 110 can be mounted, the system 100 will preferably display on command a menu of containers from which the user can select. This may be done, for example, by means of the keyboard and display 155. Each unique container configuration requires a specific adaptor into which the transducer 110 is installed. This specific adaptor must match the container that was selected from the displayed menu.

In other words, in one embodiment of the present invention the adaptor into which the transducer assembly 110 is to be installed must be one that was specifically designed for that unique container. If the adaptor does not match that container, the circuitry 150 will not allow the system 100 to be used. This sequence of events is desirable to make sure that the correct "look-up table" is selected by the circuitry 150. The circuitry will allow for an indefinite number of different "look-up" tables by programming a programmable chip or chips. This then will accommodate any new container configurations with which the system can be used by simply adding them in. A detailed description of the specific adaptor configurations which may be used in accordance with the present invention is given with reference to FIGS. 7a and 7b below.

Figure 5:
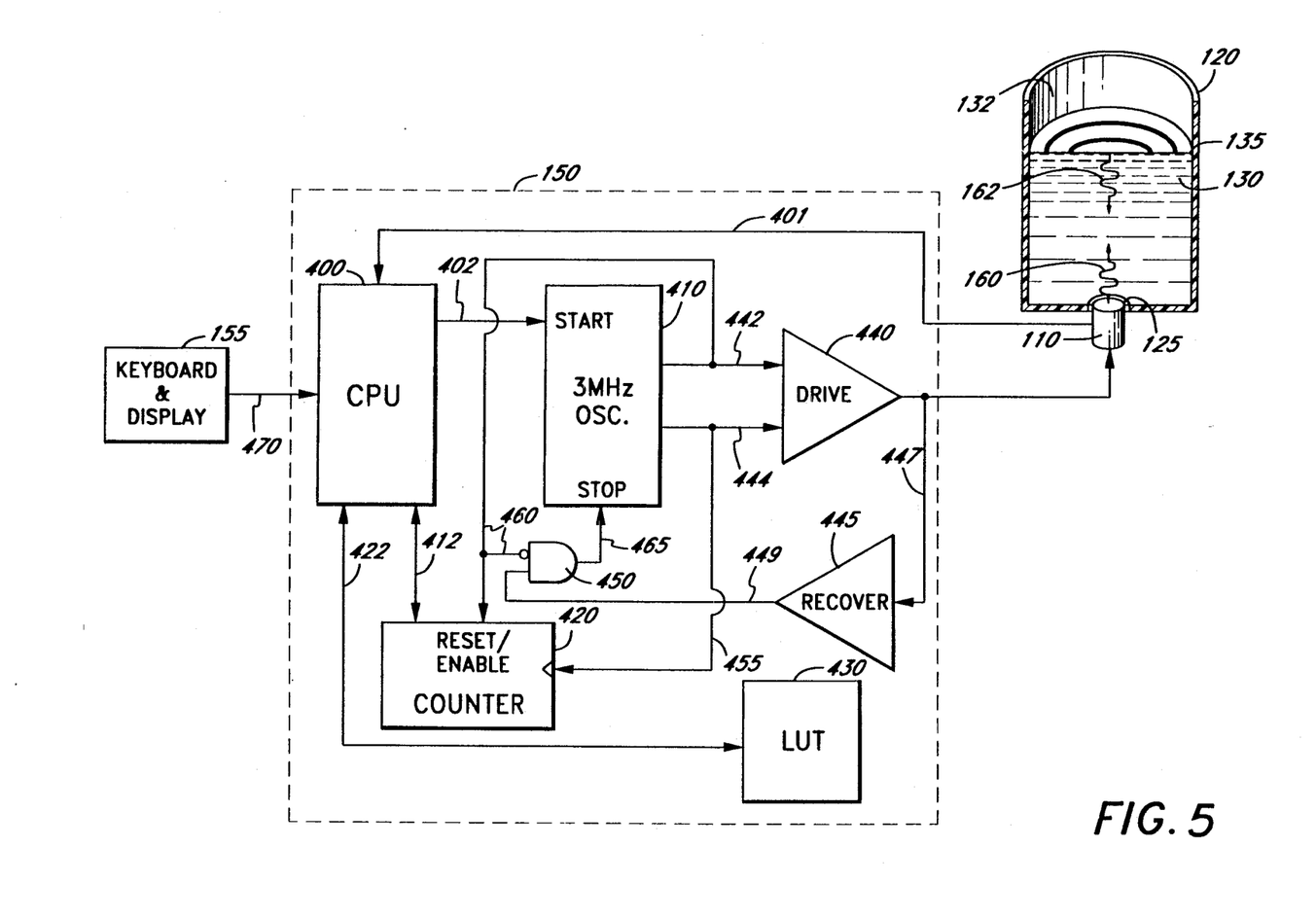
FIG. 5 is a schematic diagram showing the major components of the process and control circuitry.

FIG. 5 is a simplified block diagram which details the major functional elements of the process and control circuitry 150. The circuitry 150 includes a Central Processing Unit (CPU) 400 (e.g., Siemens 80C535 8-bit microprocessor), which is electrically connected to the transducer 110 via a line 401 and a 3 MHz oscillator 410 via a line 402. The CPU 400 is also electrically connected to a counter 420 via a bidirectional bus 412, and a look-up table memory (LUT) 430 via a bidirectional bus 422. The oscillator 410 is electrically connected to a drive amplifier 440 via an enable input line 442 and a signal input line 444. The output of the drive amplifier 440 is electrically connected to the transducer 110. The transducer 110, as well as the output of the drive amplifier 440, is electrically connected to a recover amplifier 445 via an input line 447. The output of the recover amplifier 445 is connected to a non-inverting input of an AND gate 450 via a line 449. The clock input of the counter 420 is connected to the line 444 via a line 455, and reset and enable inputs of the counter 420 are in electrical connection with the enable input line 442 via a line 460. The line 460 is also in electrical connection with an inverting input of the AND gate 450. The output of the AND gate 450 is connected to the disable input of the oscillator 410 via a line 465. Finally, the keyboard and display 155 is connected to the CPU 400 via a line 470.

Figure 6A:
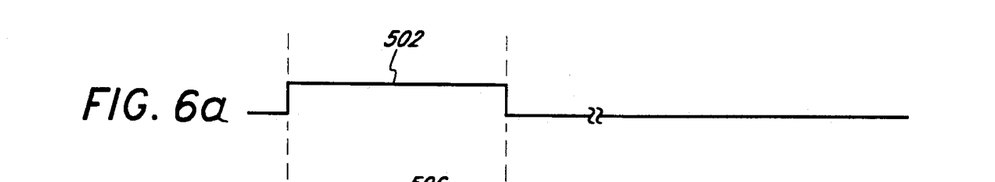
FIGS. 6a–6c are timing diagrams which show the waveshape and relative timing of certain signals produced by the electronics within the volume sensing system.
Figures 6B, 6C:
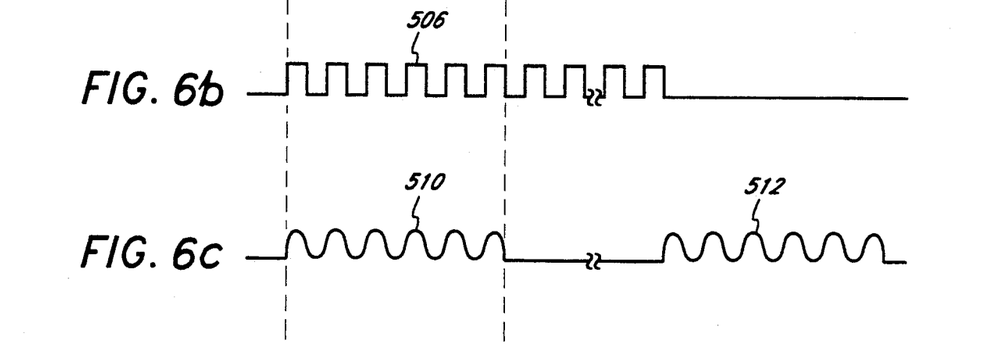

The operation of the process and control circuitry 150 will be explained with reference to the block diagram of FIG. 5 and the timing diagrams of FIGS. 6a–6c. When it is desired to determine the volume of liquid 130 within the container 120, the above-described system calibration and initialization operations are performed after the transducer 110 has been connected to the container 120 by means of the adaptor 125.

The adaptor 125 advantageously includes an indicator which may be used to identify the configuration of the container 120. For example, the adaptor 125 may include a bar code label on the surface where the transducer 110 is to be affixed. An optical arrangement, such as a photo-diode sensing device can then be incorporated into the transducer 110 as an accessory so that the photo-diode is capable of reading the bar code. The bar code advantageously includes information which may be used to identify the specific adaptor 125 so that the configuration of the container 120 is recognized by the processing circuitry 150. Once the transducer 110 is connected to the adaptor 125, a signal may be transmitted from the adaptor 125 to the CPU 400 via the transducer 110 and the line 401. The CPU 400 is pre-programmed so that the indicator signal from the adaptor 125 automatically identifies the configuration of the container 120 to which the adaptor 125 is affixed. If the configuration of the container 120 is not one which is recognizable by the system circuitry 150, then the user may input the dimensions and configuration of the container 120 manually, or a calibration procedure may be performed to install the new configuration.

After the system 100 has been calibrated and initialized, the CPU 400 transmits a signal to the oscillator 410 along the line 402 which enables the oscillator 410. Once the oscillator 410 is enabled, the oscillator 410 outputs an amplifier enable signal 502 (FIG. 6a) in synchronization with a continuous 3 MHz input signal 506 (FIG. 6b) to the drive amplifier 440 across the lines 442, 444 respectively. The enable signal 502 enables the amplifier 440 so that a signal which is applied to the input line 444 will be amplified at the output of the amplifier 440. Thus, when the enable signal 502 is high (i.e., logically active), the input signal 506 is amplified at the output of the amplifier 440. In one embodiment, the enable pulse 502 has a duration of approximately 2 microseconds, and the input signal 506 on the line 444 is a 3 MHz square wave so that six cycles of the square wave 506 are passed and amplified by the driving amplifier 440. In addition to being applied to the drive amplifier 440, the enable signal 502 is applied across the line 460 to a start input of the counter 420, and the input signal 506 is applied across the line 455 to a clock input of the counter 420. Thus, after the enable signal 502 has gone low, the counter 420 will count the number of cycles of the signal 506 until the cessation of the signal 506.

The output of the amplifier 440 is shown as the electrical pulse 510 (FIG. 6c) which is applied to the line 447. This output pulse 510 is transmitted to the transducer 110 where the electrical pulse 510 causes the crystal within the transducer 110 to vibrate at the same frequency as the signal 510 (i.e., 3 MHz). The vibration of the crystal causes the ultrasonic pulse 160 to propagate through the liquid 130 as described above with reference to FIG. 1. When the reflected "echo" pulse 162 returns, the crystal once again is caused to vibrate and produces an electrical signal pulse 512 with the same frequency as the pulse 162 on the line 447 at the input of the recover amplifier 445. Thus, the time at which the electrical pulse 510 is generated is substantially simultaneous with the generation of the ultrasonic pulse 160, and the time at which the electrical pulse 512 is generated is substantially simultaneous with the reception of the ultrasonic pulse 162.

The electrical pulse 512 is amplified and transmitted across the line 449 to the non-inverting output of the AND gate 450. Since the other input to the AND gate 450 from the line 460 is inverting, the output of the AND gate 450 will be high only when the input from the line 449 is high and the input from the line 460 is low (i.e., a logical zero). Thus, because the signal on the line 460 is the same as the signal applied to the line 442 (i.e., the enable signal 502), the output of the AND gate 450 will be high only when the enable pulse 502 is low and the signal on the line 449 is high. However, as can be seen from FIG. 6c which shows the signals 510, 512 applied to the line 447, and, after amplification, the line 449, the enable signal 502 lasts for the entire duration of the first electrical pulse 510. Therefore, the output of the AND gate 450 will first achieve a high state when the electrical pulse 512, caused by the return pulse 162 sensed by the transducer 110, is applied to the line 447 and, subsequently, the line 449.

When the output of the AND gate 450 at the line 465 is high, the oscillator 410 discontinues the output of the signal 506 along the line 444. The oscillator 410 will not resume output of the input signal 506 along the line 444 until the CPU 400 transmits another start signal to the oscillator 410 along the line 402. As stated above the counter 420 is clocked by the signal 506 so that each cycle of the signal 506 is counted by the counter 420. Moreover, when the oscillator 410 discontinues output of the signal 506, the counter 420 ceases counting. Thus, the counter 420 initiates counting at the leading edge of the enable pulse 502 and ceases counting at the first detection of a logical one at the output of the AND gate 450, that is, the counter 420 ceases counting at the first detection of the pulse 512. The number of cycles accounted for by the counter 420 is therefore the number of cycles which occur from the leading edge of the enable pulse 502 to the first detection of the signal 512 by the recover amplifier 445. However, it can be seen that the leading edge of the enable pulse 502 is synchronous with the leading edge of the first cycle of the signal 506, and, similarly the signal 510. Thus, the counter 420 accounts for the number of full cycles which occur between the leading edge of the signal 510 and the first detection of the signal 512.

Since the time between the leading edge of the signal 510 and the first detection of the electrical pulse 512 is approximately equal to the duration between the transmission and reception of the ultrasonic pulses 160, 162, the number of cycles accounted for by the counter 420 corresponds to the number of cycles generated between the transmission and reception of the ultrasonic pulses 160, 162. Thus, the total time between the generation and reception of the ultrasonic pulses 160, 162 can be calculated by multiplying the number of full cycles accounted for by the counter 420 by the period of the oscillator output. For example, if the oscillator 410 outputs a 3 MHz square wave having a period of 0.33 microseconds, and the total number of full cycles accounted for by the counter 420 is 1,000 cycles, then the time duration between the generation and reception of the pulses 160, 162 is approximately calculated as 0.33 milliseconds.

If the container 120 has an irregular configuration, then each obtained duration value will correspond to a volume value within the LUT 430. Thus, the obtained duration value is simply used to address the appropriate memory location within the LUT 430 so that the volume value stored within the addressed memory location is output to the display 155. This output volume data is updated regularly (e.g., every 50 ms) so that the user is provided with a continuous reading which indicates the volume of the liquid 130 within the irregularly shaped container 120.

If the container 120 has a known configuration, however, the duration value may be used to determine the height of the liquid 130. The height of the liquid 130 can then be used to calculate the volume of the liquid 130 within the container 120. Once the time duration between the generation and reception of the pulses 160, 162 is determined, this value can be stored as a digital value within the CPU 400 or a separate memory (not shown). The height of the liquid 130 within the container 120 can be determined by dividing the stored time value in half, to account for the distance to and from the liquid-gas boundary 135, and multiplying by the velocity value which was previously obtained during calibration of the system 100. The calculation of the height of the liquid 130 is advantageously done within the CPU 400. For example, if the stored time value is 0.33 milliseconds, and the velocity of propagation is calculated to be 3,000 feet per second, then the height of the liquid 130 within the container 120 is calculated to be $\frac{1}{2}'$, or 6". Once the height of the liquid 130 has been calculated, this value may be used to determine the volume of the liquid 130 within the container 120 having a known configuration. For example, if the container 120 is a cylinder having a base area of 100 square inches, then the total volume of the liquid 130 having a height of 6" within the container 120 is calculated to be 600 cubic inches.

Of course the description of the circuitry 150 provided above is by no means restrictive. For example, the oscillator 410 may be implemented within the CPU 400. Also, the LUT 430 may be implemented as a programmable logic array (PLA), and the AND gate 450 may be implemented as a multiplexer or other device which provides a desired output in response to a given input. Furthermore, the circuitry 150 may also include a number of buffer circuits, biasing resistors, coupling capacitors, debouncing circuits, and the like to insure smooth operation of the circuitry 150 at high frequencies. In addition, conventional circuitry to interface with the keyboard and display 155, peripherals such as a printer or a host computer, and the adaptor 125 may also be included within the circuitry 150.

The accompanying Appendix A is a detailed schematic diagram which is readily understood by one skilled in the art, and which shows each of the structural elements of the circuitry 150 in one preferred embodiment of the invention. Appendix A is hereby incorporated by reference.

Figure 7A:
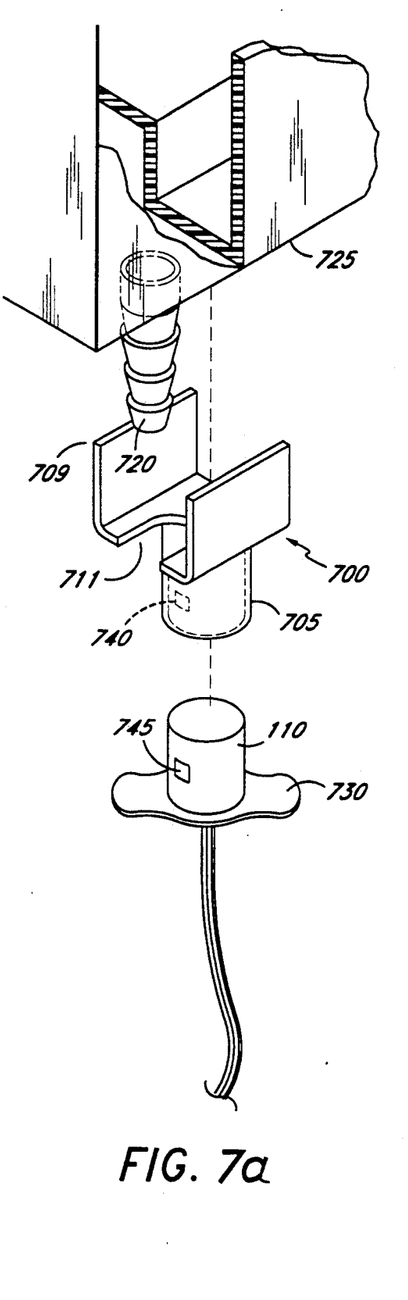
FIGS. 7a and 7b are exploded assembly views which show possible embodiments of the transducer adaptor.

FIGS. 7a and 7b are exploded assembly views which illustrate specific embodiments of adapters which may be used in connection with the transducer 110. In one embodiment shown in FIG. 7a, an adaptor 700 is made of a durable plastic, and includes a receiving member 705 which may be cylindrical or other configuration, and a connecting saddle 709. The saddle 709 has a locator notch 711 which is constructed to receive an outlet port 720 of a container 725. By situating the adaptor 700 so that the saddle 709 embraces the base of the container 725, and the notch 711 fits snugly about the outlet port 720, the adaptor 700 is effectively located proximate to the lowest point on the container 725. This is because the outlet port 720 is typically located at the lowest point of the container 725.

The cylinder 705 is constructed to receive the transducer 110 so that the transducer 110 is held firmly within the adaptor 700. Gripping members 730 are advantageously provided at the base of the transducer 110 so that a user may conveniently insert and remove the transducer 110. The adaptor 700 is also provided in some embodiments with a bar code 740 (shown in phantom) which is located on the inside surface of the cylinder 705. The transducer 110 is constructed to include a sensing photo-diode 745, which is positioned so that it coincides with the bar code 740 when the transducer 110 is secured within the adaptor 700. The photo-diode 745 is therefore capable of sensing the bar code 740 and transmitting a signal to the CPU 400 via the line 401 (FIG. 5). The signal which is transmitted to the CPU 400 indicates the model of the adaptor 700. Since the adaptor is uniquely configured to be mountable only to a specific container, this information is then used to determine the type of container 725 which is to be employed.

Figure 7B:
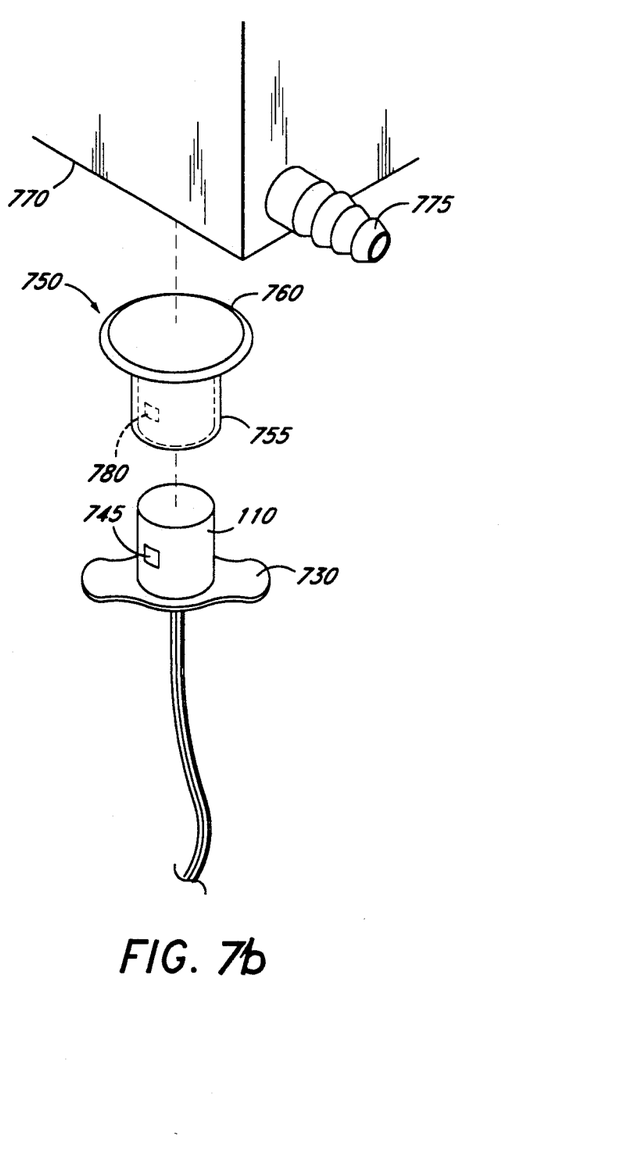

In the embodiment shown in FIG. 7b, an adaptor 750 is made of a durable plastic, and includes a receiving structure such as a cylinder 755 and a fastening surface 760. The fastening surface 760 may be attached to the base of a container 770, near an outlet port 775 by means of a suitable epoxy, two sided tape, or the like, so long as the adhesive has either minimal or no gaseous inclusions. The transducer 110 having the gripping mounts 730 and the photo-diode 745 is securable within the receiving cylinder 755. The receiving cylinder 755 also includes a bar code 780 (shown in phantom) which is situated on the inside surface of the cylinder 755. The bar code 780 is positioned so that the photo-diode 745 coincides with the bar code 780 when the transducer 110 is fastened within the cylinder 755. Thus, the photo-diode 745 is able to detect the bar code 780 by means of the electronic circuitry 150 as described above. A variety of alternatives to the bar code may be devised, as will be apparent to one of skill in the art. For example, in an embodiment where the receiving structure 755 and transducer have complementary surface structures, the location, rather than the content of the bar code or other indicator, can provide the desired information.

Machine readable identification on the adaptor is not necessary for all applications of the present invention. For example, in some instances, the adaptor will be integrally formed with the container at the point of fabrication. The transducer will be mounted on the adaptor, and the instrument calibrated all prior to sale. In this circumstance, the need to avoid adaptor-container mismatches is eliminated.

In some instances when the adaptor is separate from the container, the adaptor and container will be assembled at the point of manufacture. Assembly personnel or robotics can be supplied only with a particular container and appropriate adaptor, thereby eliminating the possibility of mismatch. Alternatively, the containers and adapters can be color coded or provided with other indicia which are human readable to insure that the appropriate adaptor and container are matched.

Machine readable indicia and/or complementary surface structures on the container and adaptor are most desirable in an embodiment intended for installation or adjustment by the end user. For example, a given adaptor may be provided with surface structures which physically prevent the attachment of that adaptor to any but corresponding surface structures on the appropriate container. These structures may take any of a variety of forms as will be readily understood by one of skill in the art. For example, one or more pins on a first surface can be required to align with one or more corresponding holes on the second surface before the first and second surfaces can be sonically engaged. Alternatively, keyways can be provided which will only receive a projection having the appropriate configuration. Also, simply conforming the adaptor mating surface to the non planar exterior of the container will work if each different volume container has a different configuration.

In a particularly preferred embodiment, the electronic circuitry 150 will also allow for the control of a number of different functions such as audible and visual alarms; a pump, to permit the filling and/or draining of the container; valves or restrictors that allow for the control of flow; and a printer, that can provide a hard copy of past activities that the level sensor/controller has completed, or print them as the activity occurs. These functions will advantageously be controlled by the CPU 400 or a peripheral host computer, so that the user may manually set, control, and monitor the parameters of the volume sensing system 100.

In one particular application, the electronic circuitry 150 will allow for the calculation of the input flow rate of the liquid 130 into the container 120. In this application, the system operator is first required to input the output flow rate of the liquid 130. This may be, for example, the infusion rate of the liquid 130 into a patient's bloodstream. The system 100 then calculates the change of the volume of the liquid 130 over a specified time interval (i.e., the rate of change of the volume of the liquid 130 within the container 120). The rate of change of the volume of the liquid 130 within the container 120 is then subtracted from the infusion rate to determine the flow rate of the liquid entering the container 120. In certain instances, this information may be desirable. For example, if the system 100 is used to recycle blood from a patient, an operator is able to tell if the patient is bleeding because the rate at which blood from the patient is reentering the container 120 is lower than the rate at which the blood is being infused into the patient's body from the container 120. In the event that a medical emergency is detected (e.g., a high rate of bleeding), an alarm may be sounded to alert the operator of the emergency.

In a preferred embodiment, the keyboard and display user interface 155 is able to output the volume of the liquid 130 remaining in the container 120, the differential volume over a selected time interval (i.e., the difference between volumes at two different times), and the time since the system has been in operation. The keyboard and display interface 155 may also be connected to a printer (not shown) which prints out data indicating trends in the volume of the liquid 130 within the container 120. These trends may be measured over five minute increments, for example. Thus, an operator is able to accurately monitor the trends of the liquid 130 within the container 120 over long periods. As stated above, this application may be advantageous in fields relating to medicine where it is important to accurately monitor the trends in a patient's fluid levels.

Figure 8:
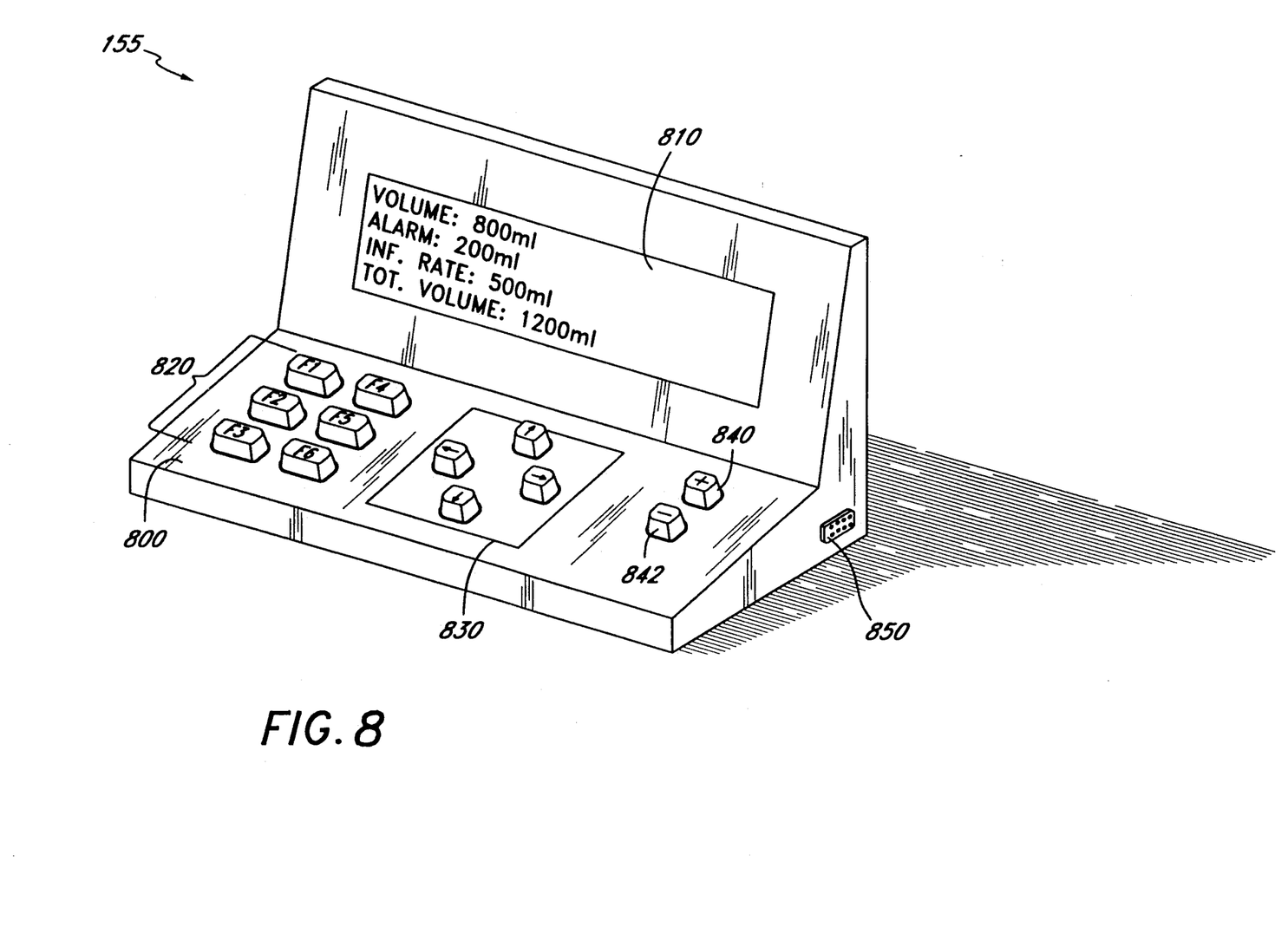
FIG. 8 is a perspective view of the keyboard and display user interface.

FIG. 8 is a perspective view which shows one embodiment of the keyboard and display user interface 155. The user interface 155 includes a keyboard 800, an LCD screen 810 and a printer connection port 815. The LCD screen 810 may be used to display such parameters as the volume of the liquid 130 within the container 120, and the low volume alarm setting. In one embodiment, the LCD screen 810 is updated every 50 ms so that the volume of the liquid 130 can be constantly monitored.

A user can input data and control the fluid volume sensing system 100 by means of the keyboard 800. In the embodiment shown, the keyboard 800 includes a plurality of function keys 820, a cursor control pad 830, and a pair of increment/decrement keys 840, 842. The function keys 820 allow the user to perform selected system functions. For example, the function keys 820 may be used to initiate calibration of the system 100, set alarm limits, input the infusion rate, and output data to a printer by means of the printer connection port 815. In addition, the function keys 820 may be used to set the time differentials for the purposes of measuring volume flow rate, or to set time increments for the purposes of trend analysis. If a user wants to set an alarm limit, for example, the user selects the appropriate function key 820. This causes an alarm limit display to appear on the LCD screen 810. The user then positions a cursor, using the cursor control pad 830, so that the cursor is directly underneath the alarm limit value it is desired to change. The alarm limit value can then be increased by depressing the increment key 840, or decreased by depressing the decrement key 842, the appropriate number of times. This method may also be used to adjust or reset any one of the controllable values displayed by the keyboard and display interface 155.

It should be noted that the fluid volume sensing system 100 may be expanded to accommodate a host computer or like equipment for expanding the processing capabilities of the system 100.

In a further embodiment of the present invention, the level sensor electronics are configured to allow the use of multiple transducers. These multiple transducers are set up in such a manner that they are activated individually for totally separate reservoirs. Thus, a first reservoir has a first transducer, a second reservoir has a second transducer, and son on as desired. The device then keeps track of the information (fluid level activity) obtained from each transducer. This information is accessible for each reservoir independently from one another, and the electronics differentiate which information belongs to which transducer or reservoir. Each transducer reservoir can be given a number or nomenclature to identify it, which can be read either on the LCD display or on the printout. The infusion rate, alarms as well as pumps or valves, can be programmed independently for each transducer.

In a further modification, the electronics are configured so that the data from the multiple transducers are combined into one. This could be useful on containers with multiple compartments that fluidically communicate with each other. These containers have compartments whose volumes would be accumulative in terms of the maximum liquid capacity that the container holds. The electronics are configured to treat each compartment as an addition or extension of the other compartment.

For example, a reservoir may have four compartments, each with a volume capacity of 500 milliliters (0.5 liter). If three compartments had 500 milliliters of liquid in them, and the fourth compartment had 300 milliliters of liquid in it, the total volume detected by the electronics for that container would be 1800 milliliters. A status could be given by the device on each compartment individually or on the combined total volume of all four compartments (the reservoir as a whole). The infusion rate, alarms, pump and valves will be activated as though a single transducer was addressed for a single reservoir. The "programming" requirements for the foregoing types of set ups will be apparent to one skilled in the art.

Fluid handling devices embodying the present invention provide significant advantages over the prior art, particularly in certain preferred medical applications. For example, in one application, the volume detector of the present invention is utilized to monitor the volume of blood drained from the chest cavity following open heart surgery. Frequently, following certain types of chest and heart surgery, a patient will be provided with a drainage tube for draining the chest cavity for a period of time following surgery. The volume of blood which is drained from the chest, and the rate at which the blood is drained, provides important feedback to the physician concerning the progress and healing, or potential necessity for re-admittance into surgery. Blood which has been drained into a container, moreover, is in some instances preferably reinfused continuously back into the patient, thereby complicating assessment of the total volume of blood drained from the chest cavity and rate of drainage. Since the rate of drainage will vary, the rate of reinfusion is frequently adjusted to roughly correlate with the rate of drainage. Generally, the rates are approximately equivalent, and, it is important that the reinfusion pump be disengaged before the blood reservoir is completely emptied.

At the present time, a nurse or other attendant manually charts "ins and outs" on an hour or other elapsed time basis depending upon the particular hospital's protocol. This charting maintains a log of the volume drained into a container (reservoir) and the volume infused, out of the container (reservoir). Unfortunately, information concerning the total volume drained can only be determined after certain calculations, which must take into account the varying drainage rates and infusion rates. This can disadvantageously delay receipt of the volume data, which may be needed quickly in an emergency situation. In addition, the total volume drained over a given time interval may be medically significant, yet cumbersome to arrive at quickly under present methods.

If the user utilizes an infusion pump that is integrally connected to the units' electronics, all 'in and out' calculations are done automatically. In addition, the units' built-in ability to print (or interface with an external printer) all the activities that have occurred, eliminates the need for 'manually' charting "in's and out's".

If, however, the user does not utilize an integrally connected infusion pump, a benefit is still accrued from the unit's built-in program that calculates the "in's and out's" for them. The user simply inputs the same infusion rate that was programmed on the external pump, into the unit. This step automatically allows the unit to compensate for fluid that is being taken out (infused) of the container (reservoir). At the touch of a button the user has access to information such as: (1) Volume drained over time (e.g. 1, 5, 15, 30, and 60 minutes); (2) Volume infused over time (e.g. 1, 5, 15, 30, and 60 minutes); and (3) Total volume drained from start of drainage (initial hook-up) to present.

In accordance with the present invention, an attendant is therefore not necessary to turn on or off the infusion pump if the reservoir volume becomes too high or low. The unit can be programmed such that it turns on an infusion pump when the volume in the reservoir has reached a sufficient level and turn the infusion pump off when the volume level is low. These 'set points' are programmable over virtually the entire volume of the container (reservoir).

If an infusion pump is utilized that does not directly interact with the electronics of the unit, the 'set points' can be used to trigger the built-in alarms. Upon reaching the user programmed 'set points', the user will be alerted visually and/or audibly, therefore allowing them to react appropriately.

The foregoing description should be construed as merely illustrative and in no way restrictive to the spirit and scope of the present invention. For example, the circuitry 150 may be implemented using specialized control and computation circuitry, or by means of computer software, rather than the CPU 400. Also, the LUT 430 may be implemented using any kind of memory unit which provides a desired output in response to a known input. Furthermore, the adaptor 125 may be implemented in a variety of embodiments which allow the transducer to be employed with any number of container configurations. Moreover, the adaptor 125 may also include a region which is permanently magnetized, or any similar means of conveying data, so that the adaptor 125 is capable of indicating the configuration of the container to which the adaptor 125 is attached. The adaptor 125 may also include electronic circuitry (e.g., an addressable memory chip) which is capable of transmitting data to the CPU via the transducer 110. Accordingly, the scope of the invention, including all embodiments and their equivalents, should be understood in light of the appended claims.

We claim:

1. An adaptor for providing an interface between a container having a predetermined configuration and a transducer for generating an ultrasonic pulse, wherein:

said adaptor is formed to affix to said container of said predetermined configuration and to said transducer so that said adaptor may be used only to connect said container and said transducer, said transducer being in sonic communication with said container when said transducer is affixed to said container by way of said adaptor, wherein said transducer generates an ultrasonic signal through said liquid in order to measure the volume of said liquid in said container; and said adaptor includes an indicator which identifies said configuration of said container to which said adaptor connects, said indicator including circuitry which is capable of transmitting data for identifying said adaptor and said predetermined configuration of said container.

2. A volume detection system for determining the volume of fluid in a container, comprising:

a container;

an indicium mechanically linked to the container for conveying information about the configuration of the container;

an ultrasonic transducer removably coupled to the container;

an indicium detector mechanically linked to the transducer, said indicium detector positioned to detect the indicium on the container; and electronics in electrical communication with said transducer and said indicium detector for identifying the container through the use of the indicium and for determining the volume of fluid in the container.

3. A volume detection system as in claim 2 further comprising an adaptor for providing an ultrasonic coupling between the transducer and the container.

4. A volume detection system as in claim 3, wherein said adaptor comprises a first unique complementary surface structure which complements a corresponding second unique surface structure on a container, so that the adaptor is only functionally mountable on a container having the second unique surface structure.

5. A volume detection system as in claim 4, wherein said indicium is disposed on the adaptor.

6. A volume detection system as in claim 5, wherein said indicium comprises a bar code.

7. A volume detection system as in claim 6, further comprising a bar code reader on the transducer for reading the bar code on the adaptor.

8. An apparatus for determining the volume of a liquid within a container having a predetermined configuration, wherein a boundary exists between said liquid and a gas, said apparatus comprising:
 a transducer in sonic communication with said container for generating and subsequently receiving an ultrasonic signal through said liquid;
 circuitry in connection with said transducer for measuring the time elapsed between the generation and reception of said ultrasonic signal;
 indicator means for indicating to said apparatus said configuration of said container, wherein said indicator means comprises a photo-diode for reading a bar code located on said container;
 circuitry for converting said elapsed time between said generation and reception of said ultrasonic signal into dimensional data; and
 means for determining volume data representing the volume of said liquid, each value of said volume data being determined from the indicated configuration of said container in combination with a value of said dimensional data.

9. A method for determining the rate of change in the volume of blood in a container having a predetermined configuration, wherein a boundary exists between said blood and a gas, said method comprising the steps of:
 (a) generating an ultrasonic signal which propagates through said blood and is subsequently received by a receiver;
 (b) measuring the time elapsed between the generation and reception of said ultrasonic signal;
 (c) converting said elapsed time between said generation and reception of said ultrasonic signal into volume data representing the volume of said blood within said container; and
 (d) repeating steps (a) to (c) a plurality of times in order to determine the change in the volume of said blood over a specified time interval, wherein an alarm is set off when said change in the volume of said blood indicates that the rate at which blood is entering said container is lower than the rate at which blood is leaving said container.

* * * * *